United States Patent [19] 
Yoo et al.

[11] Patent Number: 5,665,738
[45] Date of Patent: Sep. 9, 1997

[54] IMIDAZOLE DERIVATIVES AND PROCESSES FOR THE PREPARATION THEREOF

[75] Inventors: Sung-Eun Yoo; Kyu-Yang Yi; Sang-Hee Lee; Hye-Ryung Kim; Jee-Hee Suh; Nak-Jeong Kim; Seon-Ju Kim; Ok-Ja Cha, all of Daejeon; Young-Ah Shin, Chungjoo; Wha-Sup Shin, Daejeon; Sung-Hou Lee, Daejeon; Yi-Sook Jung, Daejeon; Byung-Ho Lee, Daejeon; Ho-Won Seo, Daejeon; Hye-Suk Lee, Daejeon, all of Rep. of Korea

[73] Assignee: Korea Research Institute of Chemical Technology, Daejeon, Rep. of Korea

[21] Appl. No.: 737,563
[22] PCT Filed: May 19, 1995
[86] PCT No.: PCT/KR95/00058
 § 371 Date: Nov. 13, 1996
 § 102(e) Date: Nov. 13, 1996
[87] PCT Pub. No.: WO95/32198
 PCT Pub. Date: Nov. 30, 1995

[30] Foreign Application Priority Data

May 21, 1994 [KR] Rep. of Korea ............ 94-11099

[51] Int. Cl.$^6$ ............ A61K 31/415; A61K 31/44; C07D 403/14
[52] U.S. Cl. ............ 514/341; 546/272.7; 546/274.4; 546/275.1
[58] Field of Search ............ 514/341; 546/272.7, 546/274.4, 275.1

[56] References Cited

U.S. PATENT DOCUMENTS 5,138,069  8/1992  Carini et al. ............ 548/253

*Primary Examiner*—Patricia L. Morris
*Attorney, Agent, or Firm*—Anderson Kill & Olick, P.C.

[57] ABSTRACT

Novel imidazole derivatives of formula(I) inhibit effectively the action of angiotensin II and have a superior antihypertensive activity:

wherein:

A is a straight, branched or cyclic $C_1-C_6$ alkyl group, or $OR_1$ wherein $R_1$ is a hydrogen, or a straight, branched or cyclic $C_1-C_6$ alkyl radical; B is a halogen, $CF_3$ or $CF_2CF_3$; X is N or N-oxide; Y is $-CH_2-$, $-CH(OR_1)-$ wherein $R_1$ is the same as defined above, or $-C(=O)-$; n is 0 or an integer of 1 to 4; Z is a halogen, $-OH$, $-OR_1$, $-NR_1R_2$, $-N(=O)R_3R_4$, $-C(=O)R_1$, $-C(=O)OR_1$, $-CH(OR_1)_2$ or $-C(=O)N_1N_2$ wherein $R_1$ is the same as defined above, $R_2$ is, independently of $R_1$, a hydrogen, or a straight, branched or cyclic $C_1-C_6$ alkyl radical, and $R_3$ and $R_4$ are independently a straight, branched or cyclic $C_1-C_6$ alkyl radical; and D is a hydrogen, or a straight, branched or cyclic $C_1-C_6$ alkyl radical.

5 Claims, No Drawings

IMIDAZOLE DERIVATIVES AND PROCESSES FOR THE PREPARATION THEREOF

FIELD OF THE INVENTION

The present invention relates to novel imidazole derivatives, processes for preparing them and pharmaceutical compositions containing same as active ingredients.

BACKGROUND OF THE INVENTION

Various imidazole derivatives, which can inhibit the action of angiotensin II, have been used for the treatment of hypertension caused by angiotensin II. Angiotensin II is produced by an angiotensin converting enzyme from angiotensin I, which is formed from angiotensinogen by the action of renin. Angiotensin II, which is a potent vasoconstrictor interacting with specific receptors on cell membrane, has been reported to cause hypertension in mammals including human beings.

Many studies have been made to search for an antagonist which inhibits the action of angiotensin II on the receptors of its target cell in order to suppress the elevation of blood pressure. As a result, many imidazole derivatives have been developed (see A. T. Chiu et al., *Eur. J. Pharm.*, 157, 13(1981); P. C. Wong et al., *J. Pharmacol. Exp. Ther.*, 247, 1(1988); and P. C. Wong et al., *Hypertension*, 13, 489(1989)).

As a representative of these compounds, for example, D. J. Carini et al. reported in *J. Med. Chem.*, 34, 2525(1990) imidazole derivatives of the following formula (A):

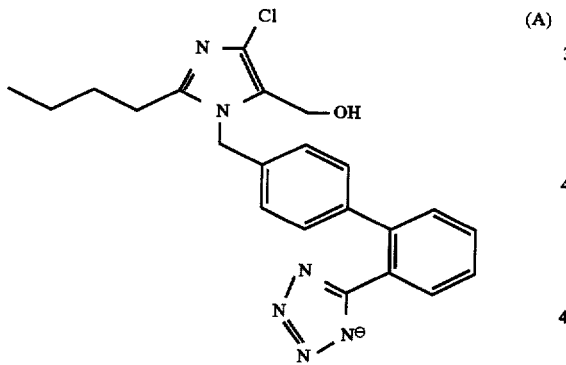

Despite these discoveries, however, needs have continued to exist for the development of more effective agents which possess enhanced antagonistic property against angiotensin II.

SUMMARY OF THE INVENTION

Accordingly, it is an object of the present invention to provide novel imidazole derivatives and pharmacologically acceptable salts thereof having an enhanced ability to suppress the activity of angiotensin II.

Another object of the present invention is to provide novel processes for preparing the inventive derivatives.

A further object of the present invention is to provide pharmaceutical compositions containing same as active ingredients.

In accordance with the present invention, there is provided novel imidazole compounds of formula (I) and pharmacologically acceptable salts thereof:

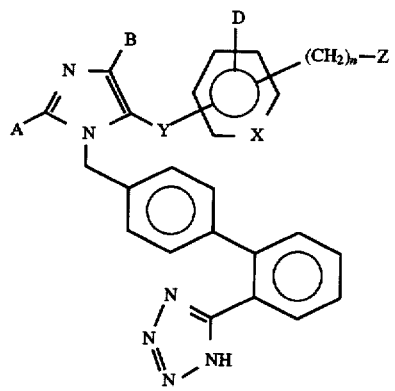

wherein:

A is a straight, branched or cyclic $C_1$–$C_6$ alkyl group, or $OR_1$ wherein $R_1$ is a hydrogen, or a straight, branched or cyclic $C_1$–$C_6$ alkyl radical;

B is a halogen, $CF_3$ or $CF_2CF_3$;

X is N or N-oxide;

Y is —$CH_2$—, —CH($OR_1$)— wherein $R_1$ is the same as defined above, or —C(=O)—;

n is 0 or an integer of 1 to 4;

Z is a halogen, —OH, —$OR_1$, —$NR_1NR_2$, —N(=O)$R_3R_4$, —C(=O)$R_1$, —C(=O)$OR_1$, —CH($OR_1$)$_2$ or —C(=O)$NR_1R_2$ wherein $R_1$ is the same as defined above, $R_2$ is, independently of $R_1$, a hydrogen, or a straight, branched or cyclic $C_1$–$C_6$ alkyl radical, and $R_3$ and $R_4$ are independently a straight, branched or cyclic $C_1$–$C_6$ alkyl radical; and D is a hydrogen, or a straight, branched or cyclic $C_1$–$C_6$ alkyl radical.

DETAILED DESCRIPTION OF THE INVENTION

Among the compounds of formula (I) of the present invention, preferred are those wherein:

A is a $C_3$–$C_5$ alkyl group;

B is Cl;

X is N or N-oxide;

Y is —CH(OH)— or —C(=O)—;

n is 0 or 1;

Z is —OH, —$NR_1R_2$, —N(=O)$R_3R_4$, —C(=O)$R_1$ or —CH($OR_1$)$_2$ wherein $R_1$ and $R_2$ are independently a hydrogen or a $C_1$–$C_3$ alkyl radical, and $R_3$ and $R_4$ are independently a $C_1$–$C_3$ alkyl radical; and D is a hydrogen, or a straight, branched or cyclic $C_1$–$C_4$ alkyl radical.

Exemplary compounds of formula (I) of the present invention are:

{2-butyl-5-chloro-3-[(2'-(1H-tetrazol-5-yl )biphenyl-4-yl)methyl]-3H-imidazol-4-yl}[6-(dimethoxymethyl)-1-oxypyridin-2-yl]methanone;

{2-butyl-5-chloro-3-[(2'-(1H-tetrazol-5-yl)biphenyl-4-yl)methyl]-3H-imidazol-4-yl}(6-formyl-1-oxypyridin-2-yl)methanone;

{2-butyl-5-chloro-3-[(2'-(1H-tetrazol-5-yl)biphenyl-4-yl)methyl]-3H-imidazol-4-yl}(6-hydroxymethyl-1-oxypyridin-2-yl)methanone;

{2-butyl-5-chloro-3-[(2'-(1H-tetrazol-5-yl)biphenyl-4-yl)methyl]-3H-imidazol-4-yl}[6-(dimethoxymethyl)pyridin-2-yl]methanone;

{2-butyl-5-chloro-3-[(2'-(1H-tetrazol-5-yl)biphenyl-4-yl)methyl]-3H-imidazol-4-yl}(6-formylpyridin-2-yl)methanone;

{2-butyl-5-chloro-3-[(2'-(1H-tetrazol-5-yl)biphenyl-4-yl)methyl]-3H-imidazol-4-yl}[6-(diethylamino)methyl-1-oxypyridin-2-yl]methanone;

{2-butyl-5-chloro-3-[(2'-(1H-tetrazol-5-yl)biphenyl-4-yl)methyl]-3H-imidazol-4-yl}[6-((diethyl)(oxy)amino)methyl-1-oxypyridin-2-yl]methanone;

{2-butyl-5-chloro-3-[(2'-(1H-tetrazol-5-yl)biphenyl-4-yl)methyl]-3H-imidazol-4-yl}[6-((diethylamino)methyl)pyridin-2-yl]methanone;

{2-butyl-5-chloro-3-[(2'-(1H-tetrazol-5-yl)biphenyl-4-yl)methyl]-3H-imidazol-4-yl}[6-(((diethyl)(oxy)amino)methyl]pyridin-2-yl]methanone;

{2-butyl-5-chloro-3-[(2'-(1H-tetrazol-5-yl)biphenyl-4-yl)methyl]-3H-imidazol-4-yl}(6-bromo-1-oxypyridin-2-yl)methanone;

{2-butyl-5-chloro-3-[(2'-(1H-tetrazol-5-yl)biphenyl-4-yl)methyl]-3H-imidazol-4-yl}[6-(1-hydroxyethyl)-1-oxypyridin-2-yl]methanone;

{2-butyl-5-chloro-3-[(2'-(1H-tetrazol-5-yl)biphenyl-4-yl)methyl]-3H-imidazol-4-yl}(6-acetyl-1-oxypyridin-2-yl)methanone;

{2-butyl-5-chloro-3-[(2'-(1H-tetrazol-5-yl)biphenyl-4-yl)methyl]-3H-imidazol-4-yl}(6-methoxycarbonyl-1-oxypyridin-2-yl)methanone;

{2-butyl-5-chloro-3-[(2'-(1H-tetrazol-5-yl)biphenyl-4-yl)methyl]-3H-imidazol-4-yl}[5-(dimethoxymethyl)-1-oxypyridin-2-yl]methanone;

{2-butyl-5-chloro-3-[(2'-(1H-tetrazol-5-yl)biphenyl-4-yl)methyl]-3H-imidazol-4-yl}(5-formyl-1-oxypyridin-2-yl)methanone;

{2-butyl-5-chloro-3-[(2'-(1H-tetrazol-5-yl)biphenyl-4-yl)methyl]-3H-imidazol-4-yl}[5-(dimethoxymethyl)pyridin-2-yl]methanone;

{2-butyl-5-chloro-3-[(2'-(1H-tetrazol-5-yl)biphenyl-4-yl)methyl]-3H-imidazol-4-yl}[5-(diethylamino)methyl-1-oxypyridin-2-yl]methanone;

{2-butyl-5-chloro-3-[(2'-(1H-tetrazol-5-yl)biphenyl-4-yl)methyl]-3H-imidazol-4-yl}[5-((diethyl)(oxy)amino)methyl-1-oxypyridin-2yl]methanone;

{2-butyl-5-chloro-3-[(2'-(1H-tetrazol-5-yl)biphenyl-4-yl)methyl]-3H-imidazol-4-yl}[5-((diethylamino)methyl)pyridin-2-yl]methanone;

{2-butyl-5-chloro-3-[(2'-(1H-tetrazol-5-yl)biphenyl-4-yl)methyl]-3H-imidazo 1-4-yl}{5-[((diethyl)(oxy)amino)methyl]pyridin-2-yl}methanone;

{2-butyl-5-chloro-3-[(2'-(1H-tetrazol-5-yl)biphenyl-4-yl)methyl]-3H-imidazol-4-yl}[6-(diethylamino)carbonyl-1-oxypyridin-2-yl]methanone;

{2-butyl-5-chloro-3-[(2'-(1H-tetrazol-5-yl)biphenyl-4-yl)methyl]-3H-imidazol-4-yl}[6-(hydroxyimino)methyl-1-oxypyridin-2-yl]methanone;

{2-butyl-5-chloro-3-[(2'-(1H-tetrazol-5-yl)biphenyl-4-yl)methyl]-3H-imidazol-4-yl}[5-(dimethoxymethyl)-6-methyl-1-oxypyridin-2-yl]methanone; and {2-butyl-5-chloro-3-[(2'-(1H-tetrazol-5-yl)biphenyl-4-yl)methyl]-3H-imidazol-4-yl}(5-formyl-6-methyl-1-oxypyridin-2-yl)methanone.

The imidazole derivatives of formula (I) of the present invention may be prepared in accordance with the procedure described below:

Pyridine or pyridine N-oxide compound of formula (II) is reacted with an alkyl lithium to produce a lithium compound of formula (II'), which is then reacted with a compound of formula (III) to give a compound of formula (IV):

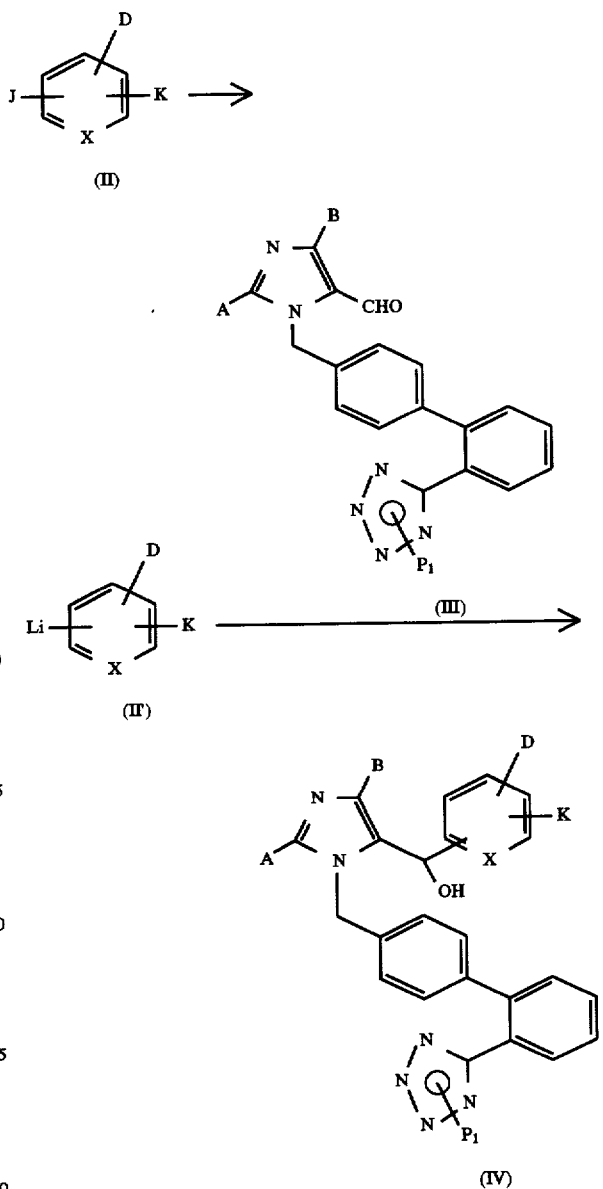

wherein:

J is Br, Cl or H;

K is —(CH$_2$)$_n$CH(OR$_1$)$_2$ or —(CH$_2$)$_n$NR$_1$R$_2$ wherein R$_1$ and R$_2$ are the same as defined previously;

P$_1$ is a tetrazole protecting group such as 1-ethoxyethyl; and

A, B, D, X and n are the same as defined previously.

Then, the compound of formula (IV) is oxidized with an oxidizing agent such as chromium trioxide, pyridium dichromate, dimethylsulfoxide-oxalyl chloride or manganese dioxide to give a compound of formula (V):

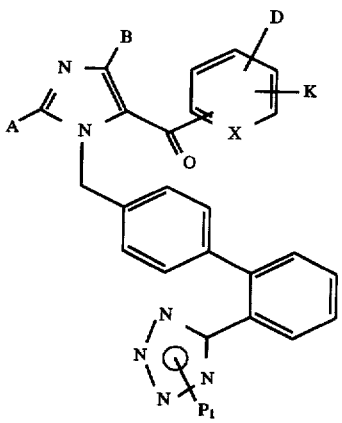

wherein A, B, D, K, $P_1$ and X are the same as defined previously.

The compound of formula (IV) or (V) is then deprotected by hydrolysis in the presence of an acid such as hydrochloric acid, sulfuric acid or toluensulfonic acid to give a compound of formula (VI) or (VII), respectively. Said reaction is carried out in a solvent such as water, water-tetrahydrofuran and alcohol.

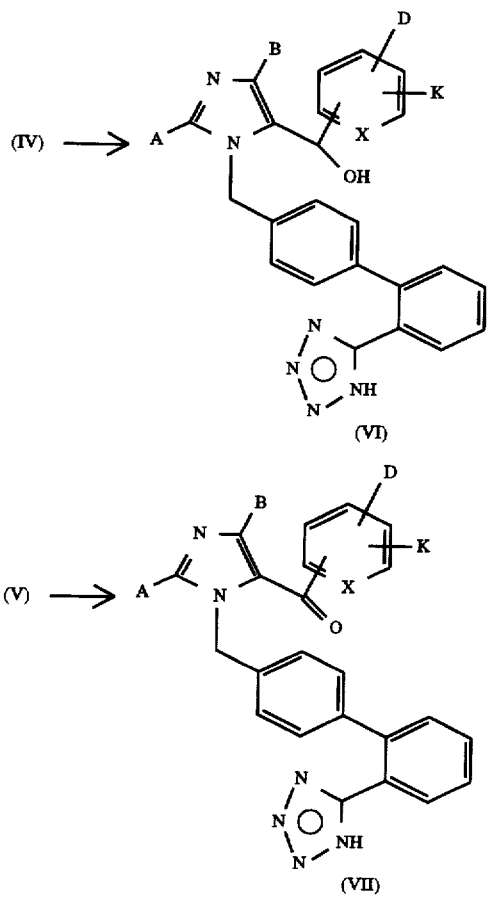

wherein A, B, D, K and X are the same as defined previously.

The compound of formula (VI) or (VII) may be converted into the imidazole derivatives of formula (I) of the present invention.

The present invention also provides pharmacologically acceptable salts, preferably, sodium or potassium salts of the compounds of formula (I) which may be prepared by a conventional method.

The novel imidazole derivatives of the present invention and pharmacologically acceptable salts thereof have an antihypertensive activity due to their antagonistic action against angiotensin II; and, therefore, may be useful for the treatment of acute or chronic cardiac deficiencies and various renal disorders as well as hypertension. The compounds of the present invention may be also useful for the treatment of migraine, Raynaud's disease and various ocular diseases caused by elevated intraocular pressure and for the prevention of the progress of atherosclerosis.

The compounds may be used alone or together with other antihypertensive agents such as a diuretic, an angiotensin converting enzyme inhibitor, a calcium-channel blocker, a potassium-channel blocker and the like.

Accordingly, the present invention also provides pharmaceutical compositions containing the compounds of formula (I) and pharmacologically acceptable salts thereof as active ingredients, and pharmaceutically acceptable carriers.

The pharmaceutical compositions of the present invention may be administered orally or parenterally. These compositions may be in a unit dosage form of tablets, capsules or powder. The pharmaceutical composition in a unit dosage may comprise about 0.1 to 1000 mg, preferably 1 to 500 mg of the active ingredient; and may be administered 4 times or less, preferably once or twice per day for an adult depending on the age and body weight of the patient, the kind and severity of the illness, and so on. The compositions of the present invention may comprise conventional adjuvants such as a filler, binder lubricant and flavoring agent. The formulation may be carried out in accordance with a conventional method.

The following Examples are intended to illustrate the present invention more specifically, without limiting the scope of the invention. The percentages as used in the Examples are by v/v, unless otherwise specified.

EXAMPLE 1

Preparation of {2-butyl-5-chloro-3-[(2'-(1H-tetrazol-5-yl)biphenyl-4-yl)methyl]-3H-imidazol-4-yl}[6-(dimethoxymethyl)-1-oxypyridin-2-yl]methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[6-(dimethoxymethyl)pyridin-2-yl]methanol 1.71 g (7.36 mmole) of 2-bromo-6-(dimethoxymethyl) pyridin was dissolved in 15 ml of tetrahydrofuran and the solution was cooled to −78° C. Thereto was added 2.65 ml (6.62 mmole) of 2.5M n-butyl lithium solution in hexane and the resultant was stirred for 30 minutes at −78° C. 1.811 g (368 mmole) of 2-butyl-4-chloro-1-[(2'-(1-(1-ethoxyethyl)-1H-tetrazol-5-yl)biphenyl-4-yl)methyl]imidazol-5-carboxyaldehyde in 20 ml of tetrahydrofuran was added to the above reaction mixture at −78° C. and stirred for 2 hours at the same temperature. 20 ml of water was added thereto and the resultant was extracted with 50 ml of ethyl acetate. The organic layer was washed with 10 ml of water, dried over anhydrous $Na_2S_4$, concentrated under reduced pressure and purified with silica gel column chromatography to obtain 1.5 g of the title compound (yield 63%).

Step 2: Preparation of {2-butyl-5-chloro-3-[(2'-(1-(1-ethoxyethyl)-1H-tetrazol-5-yl)biphenyl-4-yl)methyl]-3H-imidazol-4-yl}[6-(dimethoxymethyl)pyridin-2-yl] methanone 399.7 mg (0.619 mmole) of the compound obtained in step 1 was dissolved in 7 ml of methylene chloride and to the resulting solution was added 890 mg (10.2 mmole) of manganese dioxide. The mixture was stirred for 5 hours at room temperature and the resultant was removed from the solvent and purified with silica gel column chromatography to obtain 370 mg of the title compound (yield 93%).

Step 3: Preparation of {2-butyl-5-chloro-3-[(2'-(1-(1-ethoxyethyl)-1H-tetrazol-5-yl)biphenyl-4-yl)methyl]-3H-imidazol-4-yl}[6-(dimethoxymethyl)-1-oxypyridin-2-yl]methanone 554 mg (0.86 mmole) of tie compound obtained in step 2 was dissolved in 10 ml of methylene chloride and to the resulting solution was added 445 mg (1.29 mmole) of 3-chloroperoxybenzoic acid (50%). The mixture was stirred for 15 hours at room temperature and washed with 10 ml of aqueous sodium bicarbonate solution and 7 ml of water. The organic layer was dried over anhydrous $Na_2SO_4$, concentrated under reduced pressure and purified with silica gel column chromatography to obtain 186.8 mg of the title compound (yield 33%).

Step 4: Preparation of {2-butyl-5-chloro-3-[(2'-(1H-tetrazol-5-yl)biphenyl-4-yl)methyl]-3H-imidazol-4-yl}[6-(dimethoxymethyl)-1-oxypyridin-2-yl]methanone To 30.2 mg (0.046 mmole) of the compound obtained in step 3 was added 0.5 ml of 3% hydrogen chloride/methanol solution and the resulting solution was stirred for 5 minutes at room temperature. After being added with a small amount of sodium bicarbonate, the solution was concentrated under reduced pressure and the residue was purified with silica gel column chromatography to obtain 22.5 mg of the title compound (yield 83%).

$^1$H NMR($CD_3OD$) δ0.89(t, 3H), 1.33(m, 2H), 1.60(m, 2H), 2.70(t, 2H), 3.44(s, 6H), 5.73(s, 2H), 5.81(s, 1H), 7.15(s, 4H), 7.50–7.90(m, 7H)

EXAMPLE 2

Preparation of {2-butyl-5-chloro-3-[(2'-(1H-tetrazol-5-yl)biphenyl-4-yl)methyl]-3H-imidazol-4-yl}(6-formyl-1-oxypyridin-2-yl)methanone 186.8 mg (0.28 mmole) of the compound obtained in step 3 of Example 1 was dissolved in 3 ml of tetrahydrofuran and to the resulting solution was added 3 ml of aqueous 4N HCl solution. The resultant was stirred for 15 hours at room temperature, neutralized with aqueous 4N NaOH solution, concentrated under reduced pressure and purified with silica gel column chromatography to obtain 144 mg of the title compound (yield 95%).

$^1$H NMR($CDCl_3$) δ0.98(t, 3H), 1.50(m, 2H), 1.87(m, 2H), 1.90(t, 2H), 5.54(s, 2H), 7.15(q, 4H), 7.40–7.58(m, 5H), 7.95(t, 1H), 8.10(d, 1H)

EXAMPLE 3

Preparation of {2-butyl-5-chloro-3-[(2'-(1H-tetrazol-5-yl)biphenyl-4-yl)methyl]-3H-imidazol-4-yl}(6-hydroxymethyl-1-oxypyridin-2-yl)methanone 85.8 mg (0.158 mmole) of the compound obtained in Example 2 was dissolved in 4 ml of tetrahydrofuran and the solution was cooled to −78° C. To the resulting solution was added 0.38 ml (0.1896 mmole) of 0.5M lithium tris[(3-ethyl-3-pentyl)oxy]aluminohydride solution in tetrahydrofuran and the resultant was stirred for 1.5 hours at −78° C. Then, 0.3 ml (0.3 mmole) of aqueous 1N HCl solution was added thereto and the resulting mixture was concentrated under reduced pressure and purified with silica gel column chromatography to obtain 62.7 mg of the title compound (yield 72.8%).

$^1$H NMR($CD_3OD$) δ0.90(t, 3H), 1.34(m, 2H), 1.60(m, 2H), 2.74(t, 2H), 4.80(s, 2H), 5.76(s, 2H), 7.14(s, 4H), 7.48–7.90(m, 7H)

EXAMPLE 4

Preparation of {2-butyl-5-chloro-3-[(2'-(1H-tetrazol-5-yl)biphenyl-4-yl)methyl]-3H-imidazol-4-yl}[6-(dimethoxymethyl)pyridin-2-yl]methanol To 50 mg (0.077 mmole) of the compound obtained in step 1 of Example 1 was added 1 ml of 3% hydrogen chloride/methanol solution and the resulting solution was stirred for 10 minutes at room temperature. After being added with a small amount of $Na_2CO_3$, the resultant was concentrated under reduced pressure and purified with silica gel column chromatography to obtain 37.7 mg of the title compound (yield 85%).

$^1$H NMR($CD_3OD$) δ0.85(t, 3H), 1.30(m, 2H), 1.50(m, 2H), 2.45(t, 3H), 3.22(s, 6H), 5.23(s, 1H), 5.25(q, 2H), 6.04(s, 1H), 6.73(d, 2H), 6.99(d, 2H), 7.30–7.73(m, 7H)

EXAMPLE 5

Preparation of {2-butyl-5-chloro-3-[(2'-(1H-tetrazol-5-yl)biphenyl-4-yl)methyl]-3H-imidazol-4-yl}(6-formylpyridin-2-yl)methanol 150 mg (0.23 mmole) of the compound obtained in step 1 of Example 1 was dissolved in 3 ml of tetrahydrofuran and to the resulting solution was added 2 ml of aqueous 4N HCl solution. The resultant was stirred for 15 hours at room temperature, neutralized with aqueous 4N NaOH solution, concentrated under reduced pressure and purified with silica gel column chromatography to obtain 101 mg of the title compound (yield 83%).

$^1$H NMR(DMSO-$d_6$) δ0.80(t, 3H), 1.25(m, 2H), 1.48(m, 2H), 2.40(t, 2H), 5.23(s, 2H), 5.99(s, 1H), 6.60(d, 2H), 6.90(d, 2H), 7.10–7.90(m, 7H), 5 9.80(s, 1H)

EXAMPLE 6

Preparation of {2-butyl-5-chloro-3-[(2'-(1H-tetrazol-5-yl)biphenyl-4-yl)methyl]-3H-imidazol-4-yl}[6-(dimethoxymethyl)pyridin-2-yl]methanone To 38 mg (0.059 mmole) of the compound obtained in step 2 of Example 1 was added 1 ml of 3% hydrogen chloride/methanol solution and the resulting solution was stirred for 10 minutes at room temperature. After being added with a small amount of $Na_2CO_3$, the resultant was concentrated under reduced pressure and purified with silica gel column chromatography to obtain 26.6 mg of the title compound (yield 78.9%).

$^1$H NMR($CD_3OD$) δ0.90(t, 3H), 1.35(m, 2H), 1.60(m, 2H), 2.69(t, 2H), 3.39(s, 6H), 5.38(s, 1H), 5.58(s, 2H), 7.09(q, 4H), 7.35–7.60(m, 4H), 7.70(d, 1H), 7.79(d, 1H), 8.01(t, 1H)

EXAMPLE 7

Preparation of {2-butyl-5-chloro-3[(2'-(1H-tetrazol-5-yl)biphenyl-4-yl)methyl]-3H-imidazol-4-yl}(6-formylpyridin-2-yl)methanone 186 mg (0.289 mmole) of the compound obtained in step 2 of Example 1 was dissolved in 3 ml of tetrahydrofuran and to the resulting solution was added 2 ml of aqueous 4N HCl solution. The resultant was stirred for 15 hours at room temperature, neutralized with aqueous 4N NaOH solution, concentrated under reduced pressure and purified with silica gel column chromatography to obtain 108 mg of the title compound (yield 71%).

$^1$H NMR(DMSO-d$_6$) δ0.84(t, 3H), 1.30(m, 2H), 1.58(m, 2H), 2.70(t, 2H), 5.57(s, 2H), 7.00(d, 2H), 7.10(d, 2H), 7.39–7.60(m, 4H), 8.02(d, 1H), 8.13(d, 1H), 8.27(t, 1H), 10.00(s, 1H)

EXAMPLE 8

Preparation of {2-butyl-5-chloro-3-[(2'-(1H-tetrazol-5-yl)biphenyl-4-yl)methyl]-3H-imidazol-4-yl}[6-(hydroxymethyl)pyridin-2-yl]methanone The same procedure as in Example 3 was repeated using 56.5 mg (0.107 mmole) of the compound obtained in Example 7 to obtain 26.7 mg of the title compound (yield 47%).

$^1$H NMR(CD$_3$OD) δ0.84(t, 3H), 1.26(m, 2H), 1.54(m, 2H), 2.54(t, 2H), 4.80(s, 2H), 5.32(s, 2H), 6.86(d, 2H), 7.01(d, 2H), 7.30–7.55(m, 4H), 7.50(d, 1H), 7.79(t, 1H), 7.99(t, 1H)

EXAMPLE 9

Preparation of {2-butyl-5-chloro-3-[(2'-(1H-tetrazol-5-yl)biphenyl-4-yl)methyl]-3H-imidazol-4-yl}[6-(diethylamino)methyl-1-oxypyridin-2-yl]methanol Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[6-(diethylamino)methyl-1-oxypyridin-2-yl]methanol 352 mg (1.36 mmole) of 2-bromo-6-(diethylamino)methyl-1-oxypyridine was dissolved in 5 ml of tetrahydrofuran and the solution was cooled to –78° C. Thereto was added 0.48 ml (1.206 mmole) of 2.5M n-butyl lithium solution in hexane and the resultant was stirred for 20 minutes at –78° C. 331.5 mg (0.67 mmole) of 2-butyl-4-chloro-1-[(2'-(1-(1-ethoxyethyl)-1H-tetrazol-5-yl)biphenyl-4-yl)methyl]imidazol-5-carboxyaldehyde in 5 ml of tetrahydrofuran was added to the above reaction mixture at –78° C. and the mixture was stirred for 3 hours at the same temperature. 7 ml of aqueous sodium bicarbonate solution was added thereto and the resultant was extracted with 20 ml of ethyl acetate. The organic layer was washed with 10 ml of water, dried over anhydrous Na$_2$SO$_4$, concentrated under reduced pressure and purified with silica gel column chromatography to obtain 289 mg of the title compound (yield 64%).

Step 2: Preparation of {2-butyl-5-chloro-3-[(2'-(1H-tetrazol-5-yl)biphenyl-4-yl)methyl]-3H-imidazol-4-yl}[6-(diethylamino)methyl-1-oxypyridin-2-yl]methanol 56.1 mg (0.083 mmole) of the compound obtained in step 1 was dissolved in 1 ml of tetrahydrofuran and to the resulting solution was added 0.5 ml of aqueous 1N HCl solution. The resultant was stirred for 2.5 hours at room temperature, neutralized with aqueous 1N NaOH solution, concentrated under reduced pressure and purified with silica gel column chromatography to obtain 46 mg of the title compound (yield 92%).

$^1$H NMR(CD$_3$OD) δ0.86(t, 3H), 1.28(t, 6H), 1.30(m, 2H), 1.54(m, 2H), 2.52(t, 2H), 3.13(q, 4H), 4.34(s, 2H), 5.34(q, 2H), 6.14(s, 1H), 6.75(d, 2H), 7.04(d, 2H), 7.30–7.60(m, 6H), 8.00(d, 1H)

EXAMPLE 10

Preparation of {2-butyl-5-chloro-3-[-2'-(1H,-tetrazol-5-yl)biphenyl-4-yl)methyl]-3H-imidazol-4-yl}[6-diethylamino)methyl-1-oxypyridin-2-yl]methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[6-(diethyl amino)methyl-1-oxypyridin-2-yl]methanone 232 mg (0.34 mmole) of the compound obtained in step 1 of Example 9 was dissolved in 6 ml of methylene chloride and to the resulting solution was added 296 mg (3.4 mmole) of manganese dioxide. The resultant was stirred for 1.5 hours at room temperature and purified with silica gel column chromatography to obtain 195 mg of the title compound (yield 85.6%).

Step 2: Preparation of {2-butyl-5-chloro-3-[(2'-(1H-tetrazol-5-yl)biphenyl-4-yl)methyl]-3H-imidazo 1-4-yl}[6-(diethylamino)methyl-1-oxypyridin-2-yl]methanone 86 mg (0.128 mmole) of the compound obtained in step 1 was dissolved in 1 ml of tetrahydrofuran and to the resulting solution was added 1 ml of aqueous 1N HCl solution. The resultant was stirred for 4 hours at room temperature, neutralized with aqueous 1N NaOH solution, concentrated under reduced pressure and purified with silica gel column chromatography to obtain 71.3 mg of the title compound (yield 93%).

$^1$H NMR(CD$_3$OD) δ0.92(t, 3H), 1.32(t, 6H), 1.35(m, 2H), 1.60(m, 2H), 2.75(t, 2H), 3.15(q, 4H), 4.44(s, 2H), 5.73(s, 2H), 7.12(m, 4H), 7.40–7.90(m, 7H)

EXAMPLE 11

Preparation of {2-butyl-5-chloro-3-[(2'-(1H-tetrazol-5-yl)biphenyl-4-yl)methyl]-3H-imidazol-4-yl}[6-((diethyl)(oxy)amino)methyl-1-oxypyridin-2-yl]methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[6-((diethyl)(oxy)amino)methyl-1-oxypyridin-2-yl]methanone 58.5 mg (0.087 mmole) of the compound obtained in step 1 of Example 10 was dissolved in 3 ml of methylene chloride and to the resulting solution was added 43 mg (0.12 mmole) of 3-chloroperoxybenzoic acid (50%). The resultant was stirred for 20 minutes at room temperature, concentrated under reduced pressure and purified with silica gel column chromatography to obtain 56.6 mg of the title compound (yield 94%).

Step 2: Preparation of {2-butyl-5-chloro-3-[(2'-(1H-tetrazol-5-yl)biphenyl-4-yl)methyl]-3H-imidazol-4-yl}[6-((diethyl)(oxy)amino)methyl-1-oxypyridin-2-yl]methanone 56.6 mg (0.082 mmole) of the compound obtained in step 1 was dissolved in 1 ml of tetrahydrofuran and to the resulting solution was added 0.8 ml of aqueous 1N HCl solution. The resultant was stirred for 8 hours at room temperature, neutralized with aqueous 1N NaOH solution, concentrated under reduced pressure and purified with silica gel column chromatography to obtain 40 mg of the title compound (yield 79%).

$^1$H NMR(CD$_3$OD) δ0.80(t, 3H), 1.25(m, 2H), 1.29(t, 6H), 1.49(m, 2H), 2.60(t, 2H), 3.15(m, 2H), 3.35(m, 2H), 4.68(s, 2H), 5.62(s, 2H), 7.02(q, 4H)t 7.30–7.59(m, 6H), 7.97(d, 1H)

EXAMPLE 12

Preparation of {2-butyl-5-chloro-3-[(2'-(1H-tetrazol-5-yl)biphenyl-4-yl)methyl]-3H-imidazol-4-yl}[6-((diethylamino)methyl)pyridin-2-yl]methanol Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[6-((diethylamino)methyl)pyridin-2-yl]methanol 474 mg (1.95 mmole) of 2-bromo-6-[(diethylamino)methyl]pyridine was dissolved in 7 ml of tetrahydrofuran and the solution was cooled to –78° C. Thereto was added 0.65 ml (1.625 mmole) of 2.5M n-butyl lithium solution in hexane and the resultant was stirred for 20 minutes at −78° C. 320.5 mg (0.65 mmole) of 2-butyl-4-chloro-1-[(2'-(1-(1-ethoxyethyl)-1H-tetrazol-5-yl)biphenyl-4-yl)methyl]imidazol-5-carboxyaldehyde in 10 ml of tetrahydrofuran was added to the above reaction mixture at −78° C. and the mixture was stirred while allowing the temperature to rise slowly to −10° C. 7 ml of aqueous sodium bicarbonate solution was added thereto and the resultant was extracted with 20 ml of ethyl acetate. The organic layer was washed with 10 ml of water, dried over anhydrous $Na_2SO_4$, concentrated under reduced pressure and purified with silica gel column chromatography to obtain 113.4 mg of the title compound (yield 26.6%).

Step 2: Preparation of {2-butyl-5-chloro-3-[(2'-(1H-tetrazol-5-yl)biphenyl-4-yl)methyl]-3H-imidazol-4-yl}[6-((diethylamino)methyl)pyridin-2-yl]methanol 49.7 mg (0.076 mmole) of the compound obtained in step 1 was dissolved in 1 ml of tetrahydrofuran and to the resulting solution was added 0.5 ml of aqueous 1N HCl solution. The resultant was stirred for 8 hours at room temperature, neutralized with aqueous 1N NaOH solution, concentrated under reduced pressure and purified with silica gel column chromatography to obtain 34.4 mg of the title compound (yield 77%).

$^1$H NMR(CD$_3$OD) δ0.80(t, 3H), 1.10–1.58(m, 4H), 1.32 (t, 6H), 2.38(m, 2H), 3.15(m, 4H), 4.15(q, 2H), 5.10(d, 2H), 5.58(d, 2H), 6.20(s, 1H), 6.35(d, 2H), 6.96(d, 2H), 7.22–7.80(m, 7H)

EXAMPLE 13

Preparation of {2-butyl-5-chloro-3-[(2'-(1H-tetrazol-5-yl)biphenyl-4-yl)methyl]-3H-imidazol-4-yl}[6-((diethylamino)methyl)pyridin-2-yl]methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[6-((diethylamino)methyl)pyridin-2-yl]methanone 50 mg (0.076 mmole) of the compound obtained in step 1 of Example 12 was dissolved in 3 ml of methylene chloride and to the resulting solution was added 64.5 mg (0.152 mmole) of Des-Martin reagent. The resultant was stirred for 2 hours at room temperature and 10 ml of methylene chloride was added additionally thereto. The reaction mixture was washed with 5 ml of aqueous sodium bicarbonate solution, dried over anhydrous $Na_2SO_4$, concentrated under reduced pressure and purified with silica gel column chromatography to obtain 43.7 mg of the title compound (yield 87.8%).

Step 2: Preparation of {2-butyl-5-chloro-3-[(2'-(1H-tetrazol-5-yl)biphenyl-4-yl)methyl]-3H-imidazol-4-yl}[6-((diethylamino)methyl)pyridin-2-yl]methanone 21 mg (0.032 mmole) of the compound obtained in step 1 was dissolved in 0.5 ml of tetrahydrofuran and to the resulting solution was added 0.3 ml of aqueous 1N HCl solution. The resultant was stirred for 5 hours at room temperature, neutralized with aqueous 1N NaOH solution, concentrated under reduced pressure and purified with silica gel column chromatography to obtain 16 mg of the title compound (yield 85.8%).

$^1$H NMR(CD$_3$OD) δ0.94(t, 3H), 1.10(t, 6H), 1.38(m, 2H), 1.74(m, 2H), 2.73(t, 2H), 2.99(q, 4H), 4.10(s, 2H), 5.44(s, 2H), 6.86(d, 2H), 6.98(d, 2H), 7.28–7.68(m, 4H), 7.77(t, 1H)

EXAMPLE 14

Preparation of {2-butyl1-5-chloro-3-[(2'-(1H-tetrazol-5-yl)biphenyl-4-yl)methyl]-3H-imidazol-4-yl}[6-(((diethyl)(oxy)amino)methyl]pyridin-2-yl]methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[6-[((diethyl)(oxy)amino)methyl]pyridin-2-yl]methanone 43.7 mg (0.067 mmole) of the compound obtained in step 1 of Example 13 was dissolved in 3 ml of methylene chloride and to the resulting solution was added 27.75 mg (0.0804 mmole) of 3-chloroperoxybenzoic acid (50%). The resultant was stirred for 40 minutes at room temperature, concentrated under reduced pressure and purified with silica gel column chromatography to obtain 31.4 mg of the title compound (yield 70%).

Step 2: preparation of {2-butyl-5-chloro-3-[(2'-(1H-tetrazol-5-yl)biphenyl-4-yl)methyl]-3H-imidazol-4-yl}[6-[((diethyl)(oxy)amino)methyl]pyridin-2-yl]methanone 31 mg (0.046 mmole) of the compound obtained in step 1 was dissolved in 1 ml of tetrahydrofuran and to the resulting solution was added 0.5 ml of aqueous 1N HCl solution. The resultant was stirred for 7 hours at room temperature, neutralized with aqueous 1N NaOH solution, concentrated under reduced pressure and purified with silica gel column chromatography to obtain 21.7 mg of the title compound (yield 78.8%).

$^1$H NMR(CD$_3$OD) δ0.90(t, 3H), 1.31(t, 6H), 1.38(m, 2H), 1.52(m, 2H), 2.74(t, 2H), 3.28(q, 4H), 4.49(s, 2H), 5.58(s, 2H), 6.98(d, 2H), 7.08(d, 2H), 7.34–7.54(m, 4H), 7.82–7.92 (m, 2H), 8.05(t, 1H)

EXAMPLE 15

Preparation of {2-butyl-5-chloro-3-[(2'-(1H-tetrazol-5-yl)biphenyl-4-yl)methyl]-3H-imidazol-4-yl}(6-bromo-1-oxypyridin-2-yl)methanone.

Step 1: Preparation of {2-butyl-5-chloro-3-[(2'-(1-(1-ethoxyethyl)-1H-tetrazol-5-yl)biphenyl-4-yl)methyl]-3H-imidazol-4-yl}(6-bromo-1-oxypyridin-2-yl)methanol 228 mg (0.9 mmole) of 2,6-dibromopyridin-1-oxide was dissolved in 5 ml of tetrahydrofuran and the solution was cooled to −78° C. Thereto was added 0.32 ml (0.8 mmole) of 2.5M n-butyl lithium solution in hexane and the resultant was stirred for 30 minutes at −78° C. 90.7 mg (0.184 mmole) of 2-butyl-4-chloro-1-[(2'-(1-(1-ethoxyethyl)-1H-tetrazol-5-yl)biphenyl-4-yl)methyl]imidazol-5-carboxyaldehyde in 3 ml of tetrahydrofuran was added to the above reaction mixture at −78° C. and the mixture was stirred for 2 hours at the same temperature. 10 ml of water was added thereto and the resultant was extracted with 15 ml of ethyl acetate. The organic layer was washed with 5 ml of water, dried over anhydrous $Na_2SO_4$, concentrated under reduced pressure and purified with silica gel column chromatography to obtain 83.8 mg of the title compound (yield 70%).

Step 2: Preparation of {2-butyl-5-chloro-3-[(2'-(1-(1-ethoxyethyl)-1H-tetrazol-5-yl)biphenyl-4-yl)methyl]-3H-imidazol-4-yl}(6-bromo-1-oxypyridin-2-yl)methanone 74.3 mg (0.11 mmole) of the compound obtained in step 1 was dissolved in 3 ml of methylene chloride and to the resulting solution was added 96 mg (1.1 mmole) of manganese dioxide. The resultant was stirred for 1.5 hours at room temperature and purified with silica gel column chromatography to obtain 68 mg of the title compound (yield 93%).

Step 3: Preparation of {2-butyl-5-chloro-3-[(2'-(1H-tetrazol-5-yl)biphenyl-4-yl)methyl]-3H-imidazol-4-yl}(6-bromo-1-oxypyridin-2-yl)methanone 68 mg (0.1 mmole) of the compound obtained in step 2 was dissolved in 1 ml of tetrahydrofuran and to the resulting solution was added 0.5 ml of aqueous 1N HCl solution. The resultant was stirred for 4 hours at room temperature, neutralized with aqueous 1N NaOH solution, concentrated under reduced pressure and purified with silica gel column chromatography to obtain 52.7 mg of the title compound (yield 89%).

$^1$H NMR(CD$_3$OD) δ0.87(t, 3H), 1.32(m, 2H), 1.59(m, 2H), 2.70(t, 2H), 5.76(s, 2H), 7.17(s, 4H), 7.50–7.70(m, 2H), 8.05(m, 1H)

EXAMPLE 16

Preparation of {2-butyl-5-chloro-3-[(2'-(1H-tetrazol-5-yl)biphenyl-4-yl)methyl]-3H-imidazol-4-yl}(6-bromo-1-oxypyridin-2-yl)methanone 71.2 mg (0.107 mmole) of the compound obtained in step of Example 15 was dissolved in 1 ml of tetrahydrofuran and to the resulting solution was added 0.5 ml of aqueous 1N HCl solution. The resultant was stirred for 15 hours at room temperature, neutralized with aqueous 1N NaOH solution, concentrated under reduced pressure and purified with silica gel column chromatography to obtain 60.8 mg of the title compound (yield 95.6%).

$^1$H NMR(CD$_3$OD) δ0.85(t, 3H), 1.32(m, 2H), 1.53(m, 2H), 2.52(t, 2H), 5.33(q, 2H), 6.10(s, 1H), 6.75(d, 2H), 7.02(d, 2H), 7.20(t, 1H), 7.44–7.77(m, 5H), 7.90(d, 1H)

EXAMPLE 17

Preparation of {2-butyl-5-chloro-3-[(2'-(1H-tetrazol-5-yl)biphenyl-4-yl)methyl]-3H-imidazol-4-yl}(6-bromopyridin-2-yl)methanone The same procedures as in steps 1 to 3 of Example 15 were repeated using 260 mg (1.10 mmole) of 2,6-dibromopyridine instead of 2,6-dibromopyridine-1-oxide, and 180 mg (0.365 mmole) of 2-butyl-4-chloro-1-[(2'-(1-(1-ethoxyethyl)-1H-tetrazol-5-yl)biphenyl-4-yl)methyl]imidazol-5-carboxyaldehyde in step 1 of Example 15 to obtain 124 mg of the title compound (yield 59%).

$^1$H NMR(CD$_3$OD) δ0.90(t, 3H), 1.35(m, 2H), 1.61(m, 2H), 2.72(t, 2H), 5.57(s, 1H), 7.10(s, 4H), 7.50–7.90(m, 7H)

EXAMPLE 18

Preparation of {2-butyl-5-chloro-3-[(2'-(1H-tetrazol-5-yl)biphenyl-4-yl)methyl]-3H-imidazol-4-yl}(6-bromopyridin-2-yl)methanol The same procedure as in Example 16 was repeated using 43 mg (0.066 mmole) of the compound obtained in Example 17 to obtain 35.6 mg of the title compound (yield 93%).

$^1$H NMR(CD$_3$OD) δ0.84(t, 3H), 1.30(m, 2H), 1.50(m, 2H), 2.44(t, 2H), 5.25(q, 2H), 5.97(s, 1H), 6.64(d, 2H), 6.98(d, 2H), 7.20(d, 1H), 7.40–7.65 (m, 6H)

EXAMPLE 19

Preparation of {2-butyl-5-chloro-3-[2'-(1H-tetrazol-5-yl1)biphenyl-4-yl)methyl]-3H-imidazol-4-y1}(6-(1-hydroxyethyl)-1-oxypyridin-2-yl)methanone 41.5 mg (0.076 mmole) of the compound obtained in Example 2 was dissolved in 4 ml of tetrahydrofuran and the solution was cooled to –78° C. To the resulting solution was added 59 µl (0.177 mmole) of 3M methyl magnesium bromide solution in ethylether and the solution was stirred for 2.5 hours at –78° C. and then allowed the temperature to rise slowly to room temperature while stirring. 0.1 ml of water was added thereto and the resultant was concentrated under reduced pressure and purified with silica gel column chromatography to obtain 25.6 mg of the title compound (yield 62%).

$^1$H NMR(CD$_3$OD) δ0.87(t, 3H), 1.30(m, 2H), 1.52(d, 3H), 1.58(m, 2H), 2.70(t, 2H), 5.29(q, 1H), 5.75(s, 2H), 7.12(s, 4H), 7.42–7.88(m, 7H)

EXAMPLE 20

Preparation of {2-butyl-5-chloro-3-[(2'-(1H-tetrazol-5-yl)biphenyl-4-yl)methyl]-3H-imidazol-4-yl}(6-acetyl-1-oxypyridin-2-yl)methanone 25.6 mg (0.047 mmole) of the compound obtained in Example 19 was dissolved in 2 ml of methylene chloride and to the resulting solution was added 24 mg (0.0564 mmole) of Des-Martin reagent. The resultant was stirred for 1.5 hours at room temperature, concentrated under reduced pressure and purified with silica gel column chromatography to obtain 10.3 mg of the title compound (yield 40.5%).

$^1$H NMR(CDCl$_3$) δ0.95(t, 3H), 1.45(m, 2H), 1.79(m, 2H), 2.56(s, 3H), 2.81(t, 2H), 5.52(s, 2H), 7.08(q, 4H), 7.40–7.60 (m, 5H), 7.78(d, 2H), 7.94(d, 2H)

EXAMPLE 21

Preparation of {2-butyl-5-chloro-3-[(2'-(1H-tetrazol-5-yl1)biphenyl1-4-yl)methyl]-3H-imidazol-4-yl}(6-methoxycarbonyl-1-oxypyridin-2-yl)methanone 1 ml of the aqueous solution of 69 mg (0.3 mmole) of silver oxide and 36 mg (0.09 mmole) of NaOH was added to 1 ml of the aqueous solution of 81.6 mg (0.15 mmole) of the compound obtained in Example 2 at room temperature. The resulting mixture was stirred for 2 hours at room temperature, filtered through Celite, adjusted to pH 4 with aqueous 1N HCl solution and concentrated under reduced pressure. Thereto was added 4 ml of 3% hydrogen chloride/methanol solution and the resultant was refluxed for 2 hours, concentrated under reduced pressure and purified with silica gel column chromatography to obtain 41 mg of the title compound (yield 48%).

$^1$H NMR(CD$_3$OD) δ0.86(t, 3H), 1.30(m, 2H), 1.57(m, 2H), 2.69(t, 2H), 3.94(s, 3H), 5.74(s, 2H), 7.12(s, 4H), 7.46–7.69(m, 6H), 7.90(m, 1H)

EXAMPLE 22

Preparation {2-butyl-5-chloro-3-[(2'-(1H-tetrazol-5-yl)biphenyl-4-yl)methyl]-3H-imidazol-4-yl}[5-(dimethoxymethyl)-1-oxypyridin-2-yl]methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[5-(dimethoxymethyl)pyridin-2-yl]methanol 810 mg (3.49 mmole) of 2-bromo-5-(dimethoxymethyl)pyridine was dissolved in 8 ml of tetrahydrofuran and the solution was cooled to –78° C. Thereto was added 1.40 ml (3.49 mmole) of 2.5M n-butyl lithium solution in hexane and the resultant was stirred for 30 minutes at –78° C. 860 mg (1.74 mmole) of 2-butyl-4-chloro-1-[(2'-(1-(1-ethoxyethyl)-1H-tetrazol-5-yl)biphenyl-4-yl)methyl]imidazol-5-carboxyaldehyde in 5 ml of tetrahydrofuran was added slowly to the above reaction mixture at –78° C. and the mixture was stirred for 2 hours at the same temperature. 10 ml of water was added thereto and the resultant was extracted with 30 ml of ethyl acetate. The organic layer was washed with 10 ml of saturated NaCl solution, dried over anhydrous Na$_2$SO$_4$, concentrated under reduced pressure and purified with silica gel column chromatography to obtain 1.06 g of the title compound (yield 94%).

Step 2: Preparation of {2-butyl-5-chloro-3-[(2'-(1-(1-ethoxyethyl)-1H-tetrazol-5-yl)biphenyl-4-yl)methyl]-3H-imidazol-4-yl}[5-(dimethoxymethyl)pyridin-2-yl]methanone 500 mg (0.77 mmole) of the compound obtained in step 1 was dissolved in 8 ml of methylene chloride and to the resulting solution was added 73 mg (7.74 mmole) of manganese dioxide. The mixture was stirred for 5 hours at room temperature and the resultant was removed from the solvent and purified with silica gel column chromatography to obtain 346 mg of the title compound (yield 70%).

Step 3: Preparation of {2-butyl-5-chloro-3-[(2'-(1-(1-ethoxyethyl)-1H-tetrazol-5-yl)biphenyl-4-yl)methyl]-3H-imidazol-4-yl}[5-(dimethoxymethyl)-1-oxypyridin-2-yl]methanone 377 mg (0.59 mmole) of the compound obtained in step 2 was dissolved in 5 ml of methylene chloride and to the resulting solution was added 303 mg (0.88 mmole) of 3-chloroperoxybenzoic acid (50%). The solution was stirred for 15 hours at room temperature and 5 ml of aqueous saturated sodium bicarbonate solution was added thereto. The resultant was extracted with 20 ml of ethylacetate, washed with saturated NaCl solution, dried over anhydrous Na$_2$SO$_4$, concentrated under reduced pressure and then purified with silica gel column chromatography to obtain 256 mg of the title compound (yield 66%).

Step 4: Preparation of {2-butyl-5-chloro-3-[(2'-(1H-tetrazol-5-yl)biphenyl-4-yl)methyl]-3H-imidazol-4-yl}[5-(dimethoxymethyl)-1-oxypyridin-2-yl]methanone To 26 mg (0.039 mmole) of the compound obtained in step 3 was added 0.5 ml of 3% hydrogen chloride/methanol solution and the resulting solution was stirred for 10 minutes at room temperature. After being added with 20 mg of sodium bicarbonate, the solution was concentrated under reduced pressure and purified with silica gel column chromatography to obtain 18 mg of the title compound (yield 79%).

$^1$H NMR(CD$_3$OD) δ0.90(t, 3H), 1.35(m, 2H), 1.60(m, 2H), 2.73(t, 2H), 3.40(s, 6H), 5.58(s, 1H), 5.77(s, 2H), 7.12(d, 2H), 7.18(d, 2H), 7.52–7.78(m, 6H), 8.36(s, 1H)

EXAMPLE 23

Preparation of {2-butyl1-5-chloro-3-[(2'-(1H-tetrazol-5-yl)biphenyl-4-yl)methyl]-3H-imidazol-4-yl}(5-formyl-1-oxypyridin-2-yl)methanone The same procedure as in Example 2 was repeated using 252 mg (0.38 mmole) of the compound obtained in step 3 of Example 22 to obtain 169 mg of the title compound (yield 82%).

$^1$H NMR(CDCl$_1$) δ1.02(t, 3H), 1.54(m, 2H), 1.90(m, 2H), 2.98(t, 2H), 5.54(s, 2H), 7.09(d, 2H), 7.18(d, 2H), 7.39–7.63 (m, 4H), 7.99(d, 1H), 8.14(dd, 1H), 8.53(s, 1H)

EXAMPLE 24

Preparation of {2-butyl-5-chloro-3-[(2'-(1H-tetrazol-5-yl1)biphenyl1-4-yl)methyl1]-3H-imidazol-4-yl}(5-hydroxymethyl-1-oxypyridin-2-yl)methanol 21 mg (0.039 mmole) of the compound obtained in Example 23 was dissolved in 1 ml of methanol and to the resulting solution was added 3 mg of sodium borohydride and reacted for 30 minutes. Then, the resultant was concentrated under reduced pressure and purified with silica gel column chromatography to obtain 19 mg of the title compound (yield 89%).

$^1$H NMR(CD$_3$OD) δ0.87(t, 3H), 1.32(m, 2H), 1.54(m, 2H), 2.55(t, 2H), 4.56(s, 2H), 5.31(d, 1H), 5.49(d, 1H), 6.11(s, 2H), 6.95(d, 2H), 7.05(d, 2H), 7.43–7.74(m, 4H), 7.91(d, 1H), 7.99(dd, 1H), 8.18(d, 1H)

EXAMPLE 25

Preparation of {2-butyl-5-chloro-3-[(2'-(1H-tetrazol-5-yl)biphenyl-4-yl)methyl]-3H-imidazol-4-yl}[5-(dimethoxymethyl)pyridin-2-yl]methanol The same procedure as in step 4 of Example 22 was repeated using 34 mg (0.053 mmole) of the compound obtained in step 1 of Example 22 to obtain 28 mg of the title compound (yield 92%).

$^1$H NMR(CDCl$_3$) δ0.80(t, 3H), 1.25(m, 2H), 1.54(m, 2H), 2.29(t, 3H), 3.20(s, 3H), 3.28(s, 3H), 4.89(d, 1H), 5.12(d, 1H), 5.32(s, 1H), 5.45(s, 1H), 6.02(s, 1H), 6.53(d, 2H), 6.85(d, 2H), 7.30–7.71(m, 4H), 7.80(dd, 1H), 8.41(s, 1H), 8.62(d, 1H)

EXAMPLE 26

Preparation of {2-butyl-5-chloro-3-[(2'-(1H-tetrazol-5-yl)biphenyl-4-yl)methyl]-3H-imidazol-4-yl}[5-(dimethoxymethyl)pyridin-2-yl]methanone The same procedure as in Example 6 was repeated using 34 mg (0.053 mmole) of the compound obtained in step 2 of Example 22 to obtain 28 mg of the title compound (yield 92%).

$^1$H NMR(CD$_3$OD) δ0.92(t, 3H), 1.37(m, 2H), 1.64(m, 2H), 2.73(t, 2H), 3.39(s, 6H), 5.60(s, 1H), 5.61(s, 2H), 7.11(s, 4H), 7.48–7.70(m, 4H), 7.78(d, 1H), 8.05(dd, 1H), 8.69(d, 1H)

EXAMPLE 27

Preparation of {2-butyl-5-chloro-3-[(2'-(1H-tetrazol-5-yl1)biphenyl-4-yl)methyl]-3H-imidazol-4-yl}(5-formylpyridin-2-yl)methanone The same procedure as in Example 7 was repeated using 485 mg (0.75 mmole) of the compound obtained in step 2 of Example 22 to obtain 320 mg of the title compound (yield 81%).

$^1$H NMR(CDCl$_3$) δ0.82(t, 3H), 1.31(m, 2H), 1.63(m, 2H), 2.60(t, 3H), 5.43(s, 2H), 7.00(brs, 4H), 7.31–7.58(m, 4H), 7.78(d, 1H), 8.30(d, 1H), 9.01(s, 1H), 10.19(s, 1H)

EXAMPLE 28

Preparation of {2-butyl-5-chloro-3-[(2'-(1H-tetrazol-5-yl)biphenyl1-4-yl)methyl]-3H-imidazol-4-yl}[5-hydroxymethyl)pyridin-2-yl]methanone The same procedure as in Example 3 was repeated using 335 mg (2.64 mmole) of the compound obtained in Example 27 to obtain 189 mg of the title compound (yield 56%).

$^1$H NMR(CD$_3$OD) δ0.92(t, 3H), 1.39(m, 2H), 1.64(m, 2H), 2.75(t, 2H), 4.79(s, 2H), 5.62(s, 2H), 7.11(s, 4H), 7.48–7.67(m, 4H), 7.78(d, 1H), 8.01(dd, 1H), 8.66(d, 1H)

EXAMPLE 29

Preparation of {2-butyl-5-chloro-3-[(2'-(1H-tetrazol-5-yl)biphenyl-4-yl)methyl]-3H-imidazol-4-yl}[5-(chloromethyl)pyridin-2-yl]methanone 30 mg (0.057 mmole) of the compound obtained in Example 28 was dissolved in 1 ml of chloroform and to the resulting solution was added 4 μl (0.57 mmole) of thionyl chloride. The resultant was refluxed for 1 hour, concentrated under reduced pressure to remove the solvent and purified with silica gel column chromatography to obtain 28 mg of the title compound (yield 91%).

$^1$H NMR(CD$_3$OD) δ0.92(t, 3H), 1.38(m, 2H), 1.63(m, 2H), 2.7l(t, 2H), 4.80(s, 2H), 5.59(s, 2H), 7.12(s, 4H), 7.50–7.69(m, 4H), 7.79(d, 1H), 8.08(dd, 1H), 8.70(d, 1H)

EXAMPLE 30

Preparation of {2-butyl-5-chloro-3-[(2'-(1H-tetrazol-5-yl)biphenyl-4-yl)methyl]-3H-imidazol-4-yl}[5-(hydroxymethyl)pyridin-2-yl]methanol The same procedure as in Example 24 was repeated using 36 mg (0.068 mmole) of the compound obtained in Example 27 to obtain 31 mg of the title compound (yield 86%).

¹H NMR(CD₃OD) δ0.85(t, 3H), 1.27(m, 2H), 1.50(m, 2H), 2.43(t, 2H), 4.55(s, 2H), 5.14(d, 1H), 5.33(d, 1H), 6.07(s, 2H), 6.72(d, 2H), 6.97(d, 2H), 7.50–7.76(m, 6H), 8.34(s, 1H)

EXAMPLE 31

Preparation of {2-butyl-5-chloro-3-[(2'-(1H-tetrazol-5-yl)biphenyl-4-yl)methyl]-3H-imidazol-4-yl}[5-(diethylamino)methyl-1-oxypyridin-2-yl]methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[5-(diethylamino)methyl-1-oxypyridin-2-yl]methanol The same procedure as in step 1 of Example 9 was repeated using 342 mg (1.32 mmole) of 2-bromo-5-(diethylamino)methyl-1-oxypyridine and 325 mg (0.66 mmole) of 2-butyl-4-chloro-1-[(2'-(1-(1-ethoxyethyl)-1H-tetrazol-5-yl)biphenyl-4-yl)methyl]imidazol-5-carboxyaldehyde to obtain 280 mg of the title compound (yield 63%).

Step 2: Preparation of {2-butyl-5-chloro-3-[(2'-(1H-tetrazol-5-yl)biphenyl-4-yl)methyl]-3H-imidazol-4-yl}[5-(diethylamino)methyl-1-oxypyridin-2-yl]methanone The same procedures as in steps 1 and 2 of Example 10 were repeated using 100 mg (0.15 mmole) of the compound obtained in step 1 to obtain 65 mg of the title compound (yield 72%).

¹H NMR(CD₃OD) δ0.84(t, 3H), 1.35(t, 6H), 1.38(m, 2H), 1.50(m, 2H), 2.65(t, 2H), 4.36(s, 2H), 5.50(s, 2H), 6.92(d, 2H), 7.02(d, 2H), 7.35–7.60(m, 4H), 7.72(d, 1H), 8.04(dd, 1H), 8.67(d, 1H)

EXAMPLE 32

Preparation of {2-butyl-5-chloro-3-[(2'-(1H-tetrazol-5-yl)biphenyl-4-yl)methyl]-3H-imidazol-4-yl}[5-((diethyl)(oxy)amino)methyl-1-oxypyridin-2-yl]methanone The same procedures as in step 1 of Example 10 and steps 1 and 2 of Example 11 were repeated using 35 mg (0.052 mmole) of the compound obtained in step 1 of Example 31 to obtain 15 mg of the title compound (yield 46%).

¹H NMR(CD₃OD) δ0.82(t, 3H), 1.28(t, 6H), 1.53(m, 2H), 2.66(t, 2H), 3.21(m, 4H), 4.43(s, 2H), 5.71(s, 2H), 7.12(s, 4H)r 7.26–7.63(m, 4H), 7.75(d, 1H), 7.86(d, 1H), 8.58(s, 1H)

EXAMPLE 33

Preparation of {2-butyl-5-chloro-3-[(2'-(1H-tetrazol-5-yl)biphenyl-4-yl)methyl]-3H-imidazol-4-yl}[5-((diethylamino)methyl1)pyridin-2-yl]methanol Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[5-((diethylamino)methyl)pyridin-2-yl]methanol The same procedure as in step 1 of Example 12 was repeated using 311 mg (1.36 mmole) of 2-bromo-5-[(diethylamino)methyl]pyridin to obtain 250 mg of the title compound (yield 56%).

Step 2: Preparation of {2-butyl-5-chloro-3-[(2'-(1H-tetrazol-5-yl)biphenyl-4-yl)methyl]-3H-imidazol-4-yl}[5-((diethylamino)methyl)pyridin-2-yl]methanol The same procedure as in step 2 of Example 12 was repeated using 30 mg (0.046 mmole) of the compound obtained in step 1 to obtain 24 mg of the title compound (yield 89%).

¹H NMR(CD₃OD) δ0.84(t, 3H), 1.07(t, 6H), 1.28(m, 2H), 1.58(m, 2H), 2.44(t, 2H), 2.91(q, 4H), 4.28(s, 2H), 5.12(d, 1H), 5.59(d, 1H), 6.41(d, 2H), 6.85(d, 2H), 7.38–7.58(m, 5H), 7.83(dd, 1H), 8.45(d, 1H)

EXAMPLE 34

Preparation of {2-butyl-5-chloro-3-[(2'-(1H-tetrazol-5-yl)biphenyl-4-yl)methyl]-3H-imidazol-4-yl}[5-((diethylamino)methyl)pyridin-2-yl]methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[5-((diethylamino)methyl)pyridin-2-yl]methanone The same procedure as in step 1 of Example 13 was repeated using 180 mg (0.27 mmole) of the compound obtained in step 1 of Example 33 to obtain 153 mg of the title compound (yield 85%).

Step 2: Preparation of {2-butyl-5-chloro-3-[(2'-(1H-tetrazol-5-yl)biphenyl-4-yl)methyl]-3H-imidazol-4-yl}[5-((diethylamino)methyl)pyridin-2-yl]methanone The same procedure as in step 2 of Example 13 was repeated using 27 mg (0.041 mmole) of the compound obtained in step 1 to obtain 18 mg of the title compound (yield 75%).

¹H NMR(CD₃OD) δ0.91(t, 3H), 1.31(t, 6H), 1.36(m, 2H), 1.66(m, 2H), 2.77(t, 2H), 3.15(q, 4H), 4.39(s, 2H), 5.52(s, 2H), 6.95(d, 2H), 7.08(d, 2H), 7.38–7.55(m, 4H), 7.75(d, 1H), 8.12(dd, 1H), 5 8.72(d, 1H)

EXAMPLE 35

Preparation of {2-butyl-5-chloro-3-[(2'-(1H-tetrazol-5-yl)biphenyl1-4-yl)methyl]-3H-imidazol-4-yl}[5-[((diethyl)(oxy)amino)methyl]pyridin-2-yl]methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}{5-[((diethyl(oxy)amino)methyl]pyridin-2-yl}methanone The same procedure as in step 1 of Example 14 was repeated using 59 mg (0.09 mmole) of the compound obtained in step 1 of Example 34 to obtain 34 mg of the title compound (yield 56%).

Step 2: Preparation of {2-butyl-5-chloro-3-[(2'-(1H-tetrazol-5-yl)biphenyl-4-yl)methyl]-3H-imidazol-4-yl}{5-[((diethyl(oxy)amino)methyl]pyridin-2-yl}methanone The same procedure as in step 2 of Example 14 was repeated using 34 mg (0.051 mmole) of the compound obtained in step 1 to obtain 22 mg of the title compound (yield 72%).

¹H NMR(CD₃OD) δ0.83(t, 3H), 1.28(m, 2H), 1.35(m, 6H), 1.57(m, 2H), 2.72(t, 2H), 3.24(m, 4H), 4.47(s, 2H), 5.72(s, 2H), 7.11(s, 4H), 7.47–7.73(m, 5H), 7.90(d, 1H), 8.60(s, 1H)

EXAMPLE 36

Preparation of {2-butyl-5-chloro-3-[(2'-(1H-tetrazol-5-yl)biphenyl-4-yl)methyl]-3H-imidazol-4-yl}[6-(diethylamino)carbonyl-1-oxypyridin-2-y1]methanol Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[6-(diethylamino)carbonyl-1-oxypyridin-2-yl]methanol The same procedure as in step 1 of Example 9 was repeated using 127 mg (0.65 mmole) of 2-[(diethylamino)carbonyl]pyridine-1-oxide and 148 mg (0.3 mmole) of 2-butyl-4-chloro-1-[(2'-(1-(1-ethoxyethyl)-1H-tetrazol-5-yl)

biphenyl-4-yl)methyl]imidazol-5-carboxyaldehyde to obtain 82.8 mg of the title compound (yield 40%).

Step 2: Preparation of {2-butyl-5-chloro-3-[(2'-(1H-tetrazol-5-yl)biphenyl-4-yl)methyl]-3H-imidazol-4-yl}[6-(diethylamino)carbonyl-1-oxypyridin-2-yl]methanol The same procedure as in step 4 of Example 1 was repeated using 27.7 mg (0.04 mmole) of the compound obtained in step 1 to obtain 17.2 mg of an isomeric mixture of the title compound (yield 69%).

$^1$H NMR(CD$_3$OD) δ0.79(t, 3H), 1.00(m, 3H), 1.20(m, 5H), 1.45(m, 2H), 2.47(m, 2H), 3.06(m, 2H), 3.49(m, 2H), 5.40(m, 2H), 6.00(s, 0.5H), 6.04(s, 0.5H), 6.82(d, 1H), 7.02(d, 1H), 7.07(s, 2H), 7.50(m, 6H), 7.90(m, 1H)

EXAMPLE 37

Preparation of {2-butyl-5-chloro-3-[(2'-(1H-tetrazol-5-yl)biphenyl-4-yl)methyl]-3H-imidazol-4-yl}[6-(diethylamino)carbonyl-1-oxypyridin-2-yl] methanone Step 1: Preparation of {2-butyl-5-chloro-3-[(2'-(1-(1-ethoxyethyl)-1H-tetrazol-5-yl)biphenyl-4-yl)methyl]-3H-imidazol-4-yl}[6-(diethylamino)carbonyl-1-oxypyridin-2-yl]methanone The same procedure as in step 2 of Example 1 was repeated using 50 mg (0.073 mmole) of the compound obtained in step 1 of Example 36 to obtain 38.7 mg of the title compound (yield 77%).

Step 2: Preparation of {2-butyl-5-chloro-3-[(2'-(1H-tetrazol-5-yl)biphenyl-4-yl)methyl]-3H-imidazol-4-yl}[6-(diethylamino)carbonyl-1-oxypyridin-2-yl]methanone The same procedure as in step 4 of Example 1 was repeated using 38.7 mg (0.056 mmole) of the compound obtained in step 1 to obtain 30 mg of the title compound (yield 87%).

$^1$H NMR(CD$_3$OD) δ0.83(t, 3H), 1.10(t, 3H), 1.20(t, 3H), 1.25(m, 2H), 1.54(m, 2H), 2.66(t, 2H), 3.24(q, 2H), 3.52(m, 2H), 5.70(brs, 2H), 7.10(brs, 4H), 7.59(m, 7H)

EXAMPLE 38

Preparation of {2-butyl-5-chloro-3-[(2'-(1H-tetrazol-5-yl)biphenyl-4-yl)methyl]-3H-imidazol-4-yl-}[6-(hydroxyimino)methyl-1-oxypyridin-2-yl] methanone 27 mg (0.0497 mmole) of the compound obtained in Example 2 was dissolved in the mixture of 1 ml of methanol and 0.5 ml of water, and to the resulting solution were added 5.18 mg (0.0745 mmole) of hydroxylamine hydrochloride and 11.6 mg (0.141 mmole) of sodium acetate. The resultant was stirred for 2 hours at room temperature concentrated under reduced pressure and purified with silica gel column chromatography to obtain 18.8 mg of the title compound (yield 68%).

$^1$H NMR(CD$_3$OD) δ0.82(t, 3H), 1.28(m, 2H), 1.52(m, 2H), 2.64(t, 2H), 5.69(s, 2H), 7.10(s, 4H), 7.40–7.62(m, 6H), 8.00(d, 1H), 8.53(s, 1H)

EXAMPLE 39

Preparation of {2-butyl-5-chloro-3-[(2'-(1H-tetrazol-5-yl)biphenyl-4-yl)methyl]-3H-imidazol-4-yl}[5-(dimethoxymethyl)-6-methyl-1-oxypyridin-2-yl] methanone Step 1: Preparation of {2-butyl-5-chloro-3-[(2'-(1-(1-ethoxyethyl)-1H-tetrazol-5-yl)biphenyl-4-yl)methyl]-3H-imidazol- 4-yl}[5-(dimethoxymethyl)-6-methyl-1-oxypyridin-2-yl]methanol 486 mg (2.65 mmole) of 2-methyl-3-dimethoxymethyl-1-oxypyridine was dissolved in 9 ml of diethylether and the solution was cooled to –78° C. Thereto was added 0.97 ml (2.42 mmole) of 2.5M n-butyl lithium solution in hexane and the resultant was stirred for 30 minutes at –78° C. 664 mg (1.346 mmole) of 2-butyl-4-chloro-1-[(2'-(1-(1-ethoxyethyl)-1H-tetrazol-5-yl)biphenyl-4-yl)methyl]imidazol-5-carboxyaldehyde in 5 ml of diethylether was added to the above reaction mixture at –78° C., and the mixture was stirred for 3 hours at the same temperature and then allowed the temperature to rise slowly to room temperature while stirring. 10 ml of aqueous sodium bicarbonate solution was added thereto and the resultant was extracted with 30 ml of ethyl acetate. The organic layer was washed with 10 ml of water, dried over anhydrous Na$_2$SO$_4$, concentrated under reduced pressure and purified with silica gel column chromatography to obtain 341 mg of the title compound including other unseparated compounds, which was used in the next step as it is.

Step 2: Preparation of {2-butyl-5-chloro-3-[(2'-(1-(1-ethoxyethyl)-1H-tetrazol-5-yl)biphenyl-4-yl)methyl]-3H-imidazol-4-yl}[5-(dimethoxymethyl)-6-methyl-1-oxypyridin-2-yl]methanone.

341 mg of the compound obtained in step 1 was dissolved in 5 ml of methylene chloride and to the resulting solution was added 438 mg (5.04 mmole) of manganese dioxide. The resultant was stirred for 3 hours at room temperature and purified with silica gel column chromatography to obtain 143.5 mg of the title compound (yield 15.8%).

Step 3: Preparation of {2-butyl-5-chloro-3-[(2'-(1H-tetrazol-5-yl)biphenyl-4-yl)methyl]-3H-imidazol-4-yl}[5-(dimethoxymethyl)- 6-methyl-1-oxypyridin-2-yl] methanone To 33 mg (0.049 mmole) of the compound obtained in step 2 was added 1 ml of 3% hydrogen chloride/methanol solution and the resulting solution was stirred for 5 minutes at room temperature. After being added with a small amount of sodium bicarbonate, the solution was concentrated under reduced pressure and purified with silica gel column chromatography to obtain 24.9 mg of the title compound (yield 84%).

$^1$H NMR(CD$_3$OD) δ0.84(t, 3H), 1.28(m, 2H), 1.52(m, 2H), 2.49(s, 3H), 2.66(t, 2H), 3.35(s, 6H), 5.56(s, 1H), 5.72(s, 2H), 7.11(brs, 4H), 7.40(d, 1H), 7.44–7.68(m, 4H), 7.77(d, 2H)

EXAMPLE 40

Preparation of {2-butyl-5-chloro-3-[(2'-(1H-tetrazol-5-yl)biphenyl-4-yl)methyl]-3H-imidazol-4-yl}(5-formyl-6-methyl-1-oxypyridin-2-yl)methanone 143.5 mg (0.21 mmole) of the compound obtained in step 2 of Example 39 was dissolved in 1 ml of tetrahydrofuran and to the resulting solution was added 1 ml of aqueous 5N HCl solution. The resultant was stirred for 15 hours at room temperature, neutralized with aqueous 4N NaOH solution, concentrated under reduced pressure and purified with silica gel column chromatography to obtain 62.8 mg of the title compound (yield 54%).

$^1$H NMR(CDCl$_3$) δ1.00(t, 3H), 1.50(m, 2H), 1.85(m, 2H), 2.58(s, 3H), 2.92(t, 2H), 5.53(brs, 2H), 7.13(q, 4H), 7.40–7.62(m, 4H), 7.94(d, 1H), 8.05(dd, 1H), 10.24(s, 1H)

Activity Test

The inventive compounds were tested to measure their angiotensin II receptor binding capacity as follows.

1. Angiotensin II receptor binding assay

In accordance with the procedure disclosed in Chiu, A. T. et al., *Eur. J. Pharm.*, 157, 13 (1981)t a ligand marked with a radioistope was reacted with an angiotensin II receptor and the reactant was filtered with a glass fiber to remove unreacted ligand. After washing the filter, the amount of the remaining isotope was measured to determine the binding activity of the ligand, as described below in detail.

(i) Isolation of angiotensin II receptor

Sprague-Dawley rats and Wistar rats of 250 to 350 g (from The Korea Research Institute of Chemical Technology) were tested and the test procedures were carried out at 4° C., unless otherwise specified. Adrenal gland was separated from the Sprague-Dawley rats (liver, in the case of Wistar rats) into cortex and medulla. The separated adrenal cortex and medulla were washed with a sucrose buffer solution (0.2M sucrose, 1 mM EDTA, 10 mM Tris, pH 7.2) and homogenized in the same buffer solution by using a Teflon pestle and a Brinkmann homogenizer. The homogenates were centrifuged at 3,000× g for 10 minutes to remove precipitates and further centrifuged at 12,000× g for 13 minutes. The final supernatants were centrifuged at 102,000× g for 1 hour to obtain precipitates, which were washed with a Tris buffer solution (50 mM Tris, 5 mM $MgCl_2$, pH 7.2) and re-centrifuged at 102,000× g for 1 hour. The resulting precipitates were immediately processed at the following step or stored at −70° C.

The precipitates were suspended in a Tris buffer solution. The amount of protein was determined by using a Bio-Rad DC protein analyzing kit and the protein concentration was adjusted to the amounts of: 0.2 to 0.3 mg/ml (Sprague-Dawley rat: adrenal cortex), 1.5 to 2.0 mg/ml (Sprague-Dawley rat: adrenal medulla), and 1.5 to 2.0 mg/ml (Wistar rat: liver). To the suspension, bovine serum albumin (BSA) was added to a concentration of 0.25 wt % and the resultant was immediately processed at the following step or stored at −70° C.

(ii) Measurement of angiotensin II receptor binding capacity

50 μl (based on ligand) of [$^3$H] angiotensin II (NEN, NET-446) and 10 μl of each of the test compounds with various concentrations were added to the buffer solution (50 mM Tris (pH 7.2), 5 mM $MgCl_2$, 0.25% BSA) to adjust the final volume to be 0.5 ml. Losartan (Dup 753), which is disclosed in EP No. 400,974 issued to Merck, was used as the control compound. 100 μl of the receptor suspension was added thereto and the resulting solution was reacted for 60 minutes while stirring in a water bath at 25° C. 3 ml of cold buffer solution for analysis was added to cease the reaction. The isotope which was bound to the receptor was isolated from the resultant by using Brandel Cell Harvester System with Whatman glass fiber GF/C. After washing the filter, the radioactivity of the filter was determined by using a liquid scintillation counter. Binding inhibition (%) of the test compound was calculated as follows:

Binding Inhibition (%)=[{(T-B)−(S-B)}/(T-B)]×100 wherein T is the radioactivity (cpm) of the reaction product untreated with the test compound, S is the radioactivity (cpm) of the reaction product treated with the test compound, and B is the radioactivity (cpm) of blank test.

The results are given in Table 1.

TABLE 1

| Compound | Binding Inhibition (%) |
| --- | --- |
| 1 | 91.1 |
| 2 | 95.0 |
| 3 | 96.3 |
| 4 | 71.2 |
| 5 | 64.9 |
| 6 | 91.2 |
| 7 | 79.8 |
| 8 | 68.9 |
| 9 | 30.5 |
| 10 | 91.1 |
| 11 | 99.9 |
| 12 | 63.2 |
| 13 | 90.5 |
| 14 | 92.1 |
| 15 | 88.6 |
| 16 | 62.9 |
| 17 | 50.3 |
| 18 | 57.1 |
| 19 | 88.7 |
| 20 | 89.0 |
| 21 | 86.5 |
| 22 | 90.1 |
| 23 | 93.4 |
| 24 | 76.1 |
| 25 | 87.8 |
| 26 | 94.0 |
| 27 | 81.3 |
| 28 | 78.9 |
| 29 | 83.6 |
| 30 | 90.2 |
| 31 | 97.8 |
| 32 | 98.8 |
| 33 | 73.3 |
| 34 | 95.6 |
| 35 | 97.9 |
| 36 | 75.4 |
| 37 | 92.8 |
| 38 | 95.4 |
| 39 | 87.5 |
| 40 | 90.4 |
| Control compound (Dup 753) | 48.0 |

As can be seen from Table 1, the compounds of the present invention inhibit angiotensin II receptor binding more effectively than the control compound, which implies their antihypertensive activity.

While the invention has been described with respect to the specific embodiments, it should be recognized that various modifications and changes may be made by those skilled in the art to the invention which also fall within the scope of the invention as defined by the appended claims.

What is claimed is:

1. An imidazole compound of formula(I) and pharmacologically acceptable salts thereof:

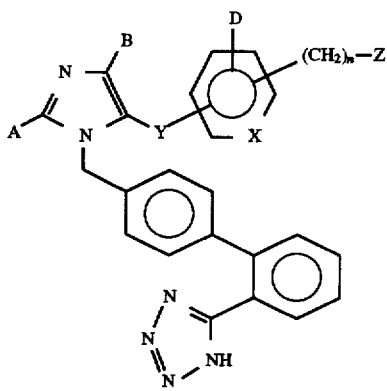

(I)

wherein:

A is a straight, branched or cyclic $C_1$-$C_6$ alkyl group, or $OR_1$ wherein $R_1$ is a hydrogen, or a straight, branched or cyclic $C_1$-$C_6$ alkyl radical;

B is a halogen, $CF_3$ or $CF_2CF_3$;

X is N or N-oxide;

Y is —$CH_2$—, —$CH(OR_1)$— wherein $R_1$ is the same as defined above, or —$C(=O)$—;

n is 0 or an integer of 1 to 4;

Z is a halogen, —OH, —$OR_1$, —$NR_1R_2$, —$N(=O)R_3R_4$, —$C(=O)R_1$, —$C(=O)OR_1$, —$CH(OR_1)_2$ or —$C(=O)NR_1R_2$ wherein $R_1$ is the same as defined above, $R_2$ is, independently of $R_1$, a hydrogen, or a straight, branched or cyclic $C_1$-$C_6$ alkyl radical, and $R_3$ and $R_4$ are independently a straight, branched or cyclic $C_1$-$C_6$ alkyl radical; and D is a hydrogen, or a straight, branched or cyclic $C_1$-$C_6$ alkyl radical.

2. The compound of claim 1 wherein A is a $C_3$-$C_5$ alkyl group; B is Cl; X is N or N-oxide; Y is —CH(OH)— or —C(=O)—; n is 0 or 1; z is —OH, —$NR_1R_2$, —$N(=O)$ $R_3R_4$, —$C(=O)R_1$ or —$CH(OR_1)_2$ wherein $R_1$ and $R_2$ are independently a hydrogen or a $C_1$-$C_3$ alkyl radical, and $R_3$ and $R_4$ are independently a $C_1$-$C_3$ alkyl radical; and D is a hydrogen, or a straight, branched or cyclic $C_1$-$C_4$ alkyl radical.

3. The compound of claim 1 which is selected from the group consisting of:

{2-butyl-5-chloro-3-[(2'-(1H-tetrazol-5-yl)biphenyl-4-yl) methyl]-3H-imidazol-4-yl}[6-(dimethoxymethyl)-1-oxypyridin-2-yl]methanone;

{2-butyl-5-chloro-3-[(2'-(1H-tetrazol-5-yl)biphenyl-4-yl) methyl]-3H-imidazol-4-yl}(6-formyl-1-oxypyridin-2-yl) methanone;

{2-butyl-5-chloro-3-[(2'-(1H-tetrazol-5-yl)biphenyl-4-yl) methyl]-3H-imidazol-4-yl}(6-hydroxymethyl-1-oxypyridin-2-yl)methanone;

{2-butyl-5-chloro-3-[(2'-(1H-tetrazol-5-yl)biphenyl-4-yl) methyl]-3H-imidazol-4-yl}[6-(dimethoxymethyl) pyridin-2-yl]methanone;

{2-butyl-5-chloro-3-[(2'-(1H-tetrazol-5-yl)biphenyl-4-yl) methyl]-3H-imidazol-4-yl}(6-formylpyridin-2-yl) methanone;

{2-butyl-5-chloro-3-[(2'-(1H-tetrazol-5-yl)biphenyl-4-yl) methyl]-3H-imidazol-4-yl}[6-(diethylamino)methyl-1-oxypyridin-2-yl]methanone;

{2-butyl-5-chloro-3-[(2'-(1H-tetrazol-5-yl)biphenyl-4-yl) methyl]-3H-imidazol-4-yl}[6-((diethyl)(oxy)amino) methyl-1-oxypyridin-2-yl]methanone;

{2-butyl-5-chloro-3-[(2'-(1H-tetrazol-5-yl)biphenyl-4-yl) methyl]-3H-imidazol-4-yl}[6-((diethylamino)methyl) pyridin-2-yl]methanone;

{2-butyl-5-chloro-3-[(2'-(1H-tetrazol-5-yl)biphenyl-4-yl) methyl]-3H-imidazol-4-yl}[6-[((diethyl)(oxy)amino) methyl]pyridin-2-yl]methanone;

{2-butyl-5-chloro-3-[(2'-(1H-tetrazol-5-yl)biphenyl-4-yl) methyl]-3H-imidazol-4-yl}(6-bromo-1-oxypyridin-2-yl) methanone;

{2-butyl-5-chloro-3-[(2'-(1H-tetrazol-5-yl)biphenyl-4-yl) methyl]-3H-imidazol-4-yl}[6-(1-hydroxyethyl)-1-2-yl] methanone;

{2-butyl-5-chloro-3-[(2'-(1H-tetrazol-5-yl)biphenyl-4-yl) methyl]-3H-imidazol-4-yl}(6-acetyl-1-oxypyridin-2-yl) methanone;

{2-butyl-5-chloro-3-[(2'-(1H-tetrazol-5-yl)biphenyl-4-yl) methyl]-3H-imidazol-4-yl}(6-methoxycarbonyl-1-oxypyridin-2-yl)methanone;

{2-butyl-5-chloro-3-[(2'-(1H-tetrazol-5-yl)biphenyl-4-yl) methyl]-3H-imidazol-4-yl}[5-(dimethoxymethyl)-1-oxypyridin-2-yl]methanone;

{2-butyl-5-chloro-3-[(2'-(1H-tetrazol-5-yl)biphenyl-4-yl) methyl]-3H-imidazol-4-yl}(5-formyl-1-oxypyridin-2-yl) methanone;

{2-butyl-5-chloro-3-[(2'-(1H-tetrazol-5-yl)biphenyl-4-yl) methyl]-3H-imidazol-4-yl}[5-(dimethoxymethyl) pyridin-2-yl]methanone;

{2-butyl-5-chloro-3-[(2'-(1H-tetrazol-5-yl)biphenyl-4-yl) methyl]-3H-imidazol-4-yl}[5-(diethylamino)methyl-1-oxypyridin-2-yl]methanone;

{2-butyl-5-chloro-3-[(2'-(1H-tetrazol-5-yl)biphenyl-4-methyl]-3H-imidazo-4-yl}[5-((diethyl)(oxy)amino) methyl-1-oxypyridin-2-yl]methanone;

{2-butyl-5-chloro-3-[(2'-(1H-tetrazol-5-yl)biphenyl-4-yl) methyl]-3H-imidazol-4-yl}(5-((diethylamino)methyl) pyridin-2-yl}methanone;

{2-butyl-5-chloro-3-[(2'-(1H-tetrazol-5-yl)biphenyl-4-yl) methyl]-3H-imidazol-4-yl}{5-[((diethyl)(oxy)amino) methyl]pyridin-2-yl}methanone;

{2-butyl-5-chloro-3-[(2'-(1H-tetrazol-5-yl)biphenyl-4-yl) methyl]-3H-imidazo-4-yl}[6-(diethylamino)carbonyl-1-oxypyridin-2-yl]methanone;

{2-butyl-5-chloro-3-[(2'-(1H-tetrazol-5-yl)biphenyl-4-yl) methyl]-3H-imidazol-4-yl}[6-(hydroxyimino)methyl-1-oxypyridin-2-yl]methanone;

{2-butyl-5-chloro-3-[(2'-(1H-tetrazol-5-yl)biphenyl-4-yl) methyl]-3H-imidazol-4-yl}[5-(dimethoxymethyl)-6-methyl-1-oxypyridin-2-yl]methanone;

{2-butyl-5-chloro-3-[(2'-(1H-tetrazol-5-yl)biphenyl-4-yl) methyl]-3H-imidazol-4-yl}(5-formyl-6-methyl-1-oxypyridin-2-yl)methanone; and mixtures thereof.

4. A process for preparing a compound of formula(I) which comprises:

(a) reacting a compound of formula(II) with an alkyl lithium to produce a compound of formula(II');

(b) reacting the compound of formula(II') with a compound of formula(III) to give a compound of formula (IV);

(c) oxidizing the compound of formula(IV) to give a compound of formula(V);

(d) deprotecting the compound of formula(IV) or (V) to give a compound of formula(VI) or (VII), respectively; and (e) converting the compound of formula(VI) or (VII) to produce the compound of formula(I)

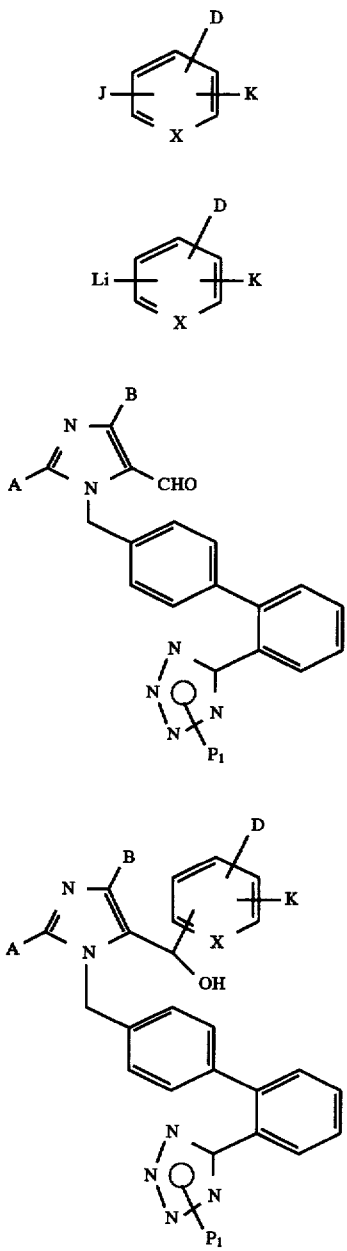

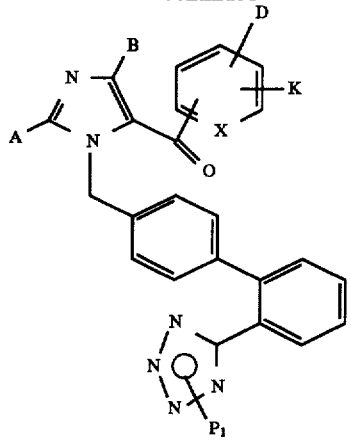

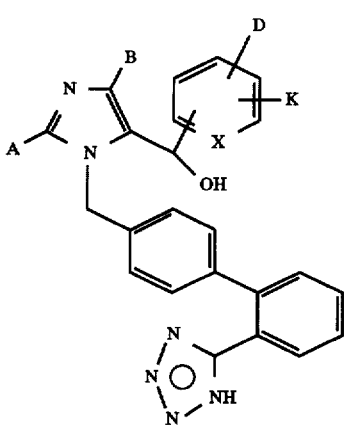

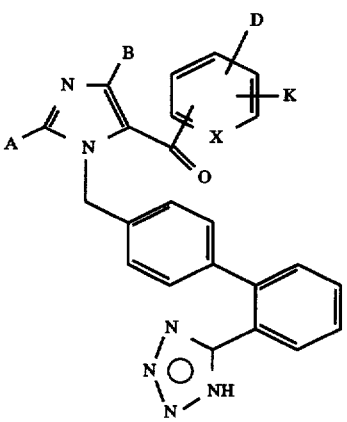

wherein:
J is Br, Cl or H;
K is —(CH$_2$)$_n$CH(OR$_1$)$_2$ or —(CH$_2$)$_n$NR$_1$R$_2$ wherein R$_1$ and R$_2$ are the same as defined in claim 1;
P$_1$ is a tetrazole protecting group; and
A, B, D, X and n are the same as defined in claim 1.

5. A pharmaceutical composition comprising a therapeutically effective amount of the imidazole compound of claim 1 and a pharmaceutically acceptable carrier or adjuvant.

* * * * *